(12) United States Patent
Yano et al.

(10) Patent No.: US 7,786,140 B2
(45) Date of Patent: Aug. 31, 2010

(54) PIPERIDINE DERIVATIVE HAVING NMDA RECEPTOR ANTAGONISTIC ACTIVITY

(75) Inventors: Toshisada Yano, Osaka (JP); Toshiyuki Kanemasa, Koka (JP); Shoichi Yamamoto, Koka (JP)

(73) Assignee: Shionogi & Co., Ltd., Osaka (JP)

( * ) Notice: Subject to any disclaimer, the term of this patent is extended or adjusted under 35 U.S.C. 154(b) by 961 days.

(21) Appl. No.: 10/573,386

(22) PCT Filed: Sep. 22, 2004

(86) PCT No.: PCT/JP2004/013775

§ 371 (c)(1),
(2), (4) Date: Nov. 13, 2006

(87) PCT Pub. No.: WO2005/030720

PCT Pub. Date: Apr. 7, 2005

(65) Prior Publication Data

US 2007/0082927 A1    Apr. 12, 2007

(30) Foreign Application Priority Data

Sep. 25, 2003   (JP) ............................. 2003-332629

(51) Int. Cl.
*A61K 31/445* (2006.01)
*C07D 211/26* (2006.01)

(52) U.S. Cl. .................. 514/317; 514/326; 546/207; 546/229

(58) Field of Classification Search .................. 514/317, 514/326; 546/207, 229
See application file for complete search history.

(56) References Cited

U.S. PATENT DOCUMENTS

| | | | |
|---|---|---|---|
| 2,973,365 A | 2/1961 | Janssen | |
| 4,232,158 A | 11/1980 | Shepard et al. | |
| 5,338,754 A | 8/1994 | Chenard | |
| 5,710,168 A | 1/1998 | Chenard | |
| 5,889,026 A | 3/1999 | Alanine et al. | |
| 7,435,744 B2 * | 10/2008 | Domany et al. | 514/321 |

FOREIGN PATENT DOCUMENTS

| | | | |
|---|---|---|---|
| EP | 0 648 744 | | 4/1995 |
| FR | 2105119 | * | 9/1970 |
| GB | 881894 | | 11/1961 |
| JP | 61-36262 | | 2/1986 |
| WO | WO 91/08200 | | 6/1991 |
| WO | WO 96/02250 | | 2/1996 |
| WO | 02/30422 | * | 4/2002 |
| WO | WO 03/035641 | | 5/2003 |

OTHER PUBLICATIONS

Collino et al. "Mannich keto basies . . . " CA 100:79478 (1984).*
Seddon "Pseudopolymorph . . . " Crystal growth and design 496) p. 1087 (2004)(2 pages from internet).*
Solvate definition from online dictionary (2009).*
Braga et al. "Making crystal from crystals . . . " J. Roy. soc, chem. chem. Commun. p. 3635-3645 (2005).*
Pinard et al. "Discovery of . . . " Bioorg. Med. Chem. Lett. v.11 p. 2173-2176 (2001).*
Yamazaki et al., "Cloning, expression and modulation of a mouse NMDA receptor subunit," FEBS Letters, vol. 300, No. 1, pp. 39-45, Mar. 1992.
Meguro et al., "Functional characerization of a heteromeric NMDA receptor channel expressed from cloned cDNAs," Nature, vol. 357, pp. 70-74, May 1992.
McGreer et al., "Duplication of biochemical changes of Huntington's chorea by intrastriatal injections of glutamic and kainic acids," Nature, vol. 263, pp. 517-519, Oct. 1976.
Turski et al., "Protection of substantia nigra from MPP+ neurotoxicity by N-methyl-D-aspartate antagonists," Nature, vol. 349, pp. 414-418, Jan. 1991.
"Academic Standards in Italy," Nature, vol. 358, p. 364, Jul. 1992.
Monyer et al., "Heteromeric NMDA Receptors: Molecular and Functional Distinction of Subtypes," Science, vol. 256, pp. 1217-1221, May 1992.
Di et al, "Effect of CP101,606, a Novel NR2B Subunit Antagonist of the N-Methyl-D-Aspartate Receptor, on the Volume of Ischemic Brain Damage and Cytotoxic Brain Edema After Middle Cerebral Artery Occlusion in the Feline Brain," Stroke, vol. 28, No. 11, pp. 2244-2251, Nov. 1997.
Chizh et al., "NMDA receptor antagonists as analgesics: focus on the NR2B subtype," Trends in Pharmacological Sciences, vol. 22, No. 12, pp. 636-642, Dec. 2001.
English translation of International Preliminary Report on Patentability issued in PCT/JP2004/013775.
Narita et al., "Mechanisms of morphine-induced rewarding effect: involvement of NMDA receptor subunits," Folia Pharmacol. Jpn., vol. 117, pp. 13-19, 2001, Abstract.
Supplementary European Search Report issued in EP 04787958 dated Nov. 6, 2008, 3 pages.
Harper, N. "Some basic ketones with central nervous system depressant activity," *Journal of Pharmacy and Pharmaceutical Sciences*, 18:3; 150-160 (1966).

* cited by examiner

*Primary Examiner*—Celia Chang
(74) *Attorney, Agent, or Firm*—Finnegan, Henderson, Farabow, Garrett & Dunner LLP

(57) ABSTRACT

A piperidine derivative of the formula (I) is found to bind specifically with the NR1/NR2B receptor and usable as an analgesic (pain treatment drug).

[Chemical Formula 1]

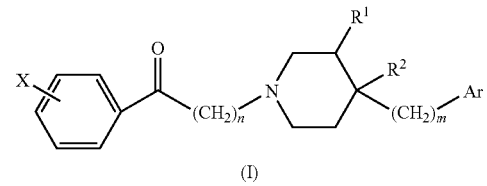

(I)

wherein X is OH or lower alkylsulfonyloxy; Ar is optionally substituted aryl or optionally substituted heteroaryl; n is an integer of 1 to 4; m is an integer of 0 to 1; $R^1$ is hydrogen; $R^2$ is OH or $R^1$ and $R^2$ taken together may form a single bond; excluding that
1) n is 2; m is 0; $R^1$ and $R^2$ taken together may form a single bond; and Ar is optionally substituted phenyl and
2) n is 3; m is 0; $R^1$ and $R^2$ taken together may form a single bond; and Ar is phenyl.

18 Claims, No Drawings

PIPERIDINE DERIVATIVE HAVING NMDA RECEPTOR ANTAGONISTIC ACTIVITY

FIELD OF THE INVENTION

The present invention relates to piperidine derivatives showing specific antagonism to glutamate receptors in a central nervous cell, particularly to NR1/NR2B receptor, which is one of NMDA receptors, causes slight side effects to the motor functions (e.g. paresthesia), psychosis (e.g. schizophrenia), and useful as a medicament such as an analgesic.

BACKGROUND OF THE INVENTION

Amino acids such as L-glutamic acid, L-aspartic acid are important as neurotransmitters for activation of nerve cells in central nervous system. However, excess accumulation of these excitatory amino acids in the exterior of the cells induces excess excitation of the nerve cells and is supposed to cause various cranial nervous diseases such as Parkinson's disease, senile dementia, Huntington chorea, and epilepsy as well as deletion of psychogenic and motor functions observed at the time of atmospheric hypoxia, ischemia and hypoglycemia, and head and spinal cord damages (reference to Non-patent Documents Nos. 1 and 2).

It has been known that the above-mentioned excitatory amino acids activate the central nerve cells through glutamate receptors existing in the nerve cells. Accordingly, the substances competitive with the excitatory amino acids for the binding to such receptors are supposed to be efficacious as medicaments for the diseases and symptoms as, for example, antiepileptic, ischemic cerebral damage preventive drugs, and antiparkinsonism drugs. Particularly, since a large quantity of glutamate is released by cranial ischemia such as cerebral infarction, the substances competitive for the glutamate receptors are supposed to be efficacious as the medicaments for an acute stage of cerebral infarction or the medicaments for chronic nerve degeneration diseases such as Alzheimer's disease.

The above-mentioned glutamate receptors can be classified into ionotropic and metabotropic receptors and theionotropic receptors can further be classified into three kinds based on the selectivity to agonists. They are called respectively as N-methyl-D-aspartic acid (NMDA) receptor, 2-amino-3-(3-hydroxy-5-methylisoxazol-4-yl)propanoic acid (AMPA) receptor, and kainate receptor.

Among them, the NMDA receptor is selectively activated by agonists such as glutamate, NMDA, ibotenic acid. The strong stimulus of the NMDA receptor induces large quantity of calcium influx to nerve cells and it is supposed to be one of causes of nerve degeneration cell death. Recently, cloning of genes of the NMDA receptor has been done from brains of rats and mice to make it clear that the NMDA receptor is composed of two subunits of NR1 and NR2 (reference to Non-patent Documents Nos. 3 and 4). The NR2 subunit contains four subfamilies (NR2A, 2B, 2C, and 2D) (reference to Non-patent Document Nos. 5 and 6). It is said that the NR1/NR2A receptors are mainly relevant to development of memory and learning acquirement and that the NR1/NR2B receptor is mainly relevant to nerve degeneration cell death and transmittance of pains (reference to Non-patent Document Nos. 7 and 8).

Those conventionally known as NMDA receptor antagonists are 1) drugs for binding to the subfamilies of the NR1/NR2 receptor competitively with agonists such as glutamate and NMDA (hereinafter, referred to as competitive NMDA receptor antagonists, e.g. D-2-amino-5-phosphonovaleric acid) and 2) drugs for inhibiting calcium influx in nerve cells by non-competitive binding to the NMDA receptor irrelevantly to the agonist such as glutamate and NMDA (hereinafter, referred to as non-competitive NMDA receptor antagonists, e.g. MK-801 (Patent Document No. 2)).

However, since the competitive NMDA receptor antagonists may possibly antagonize not only the NR1/NR2B receptor but also NR1/NR2A receptor, in the case of long time administration of the drugs for Alzheimer's disease or the like, there is a risk of deterioration of learning capability and memory formation.

Also, in recent years, morphine has been used widely for the treatment of cancer pains and other analgesics and adjuvant analgesics drugs have been used for alleviating the pains on which morphine is not efficacious and suppressing the side effects (Non-patent Document No. 9)

Ketamine is known as such an analgesic and since it is a non-competitive NMDA receptor antagonist, it is known that ketamine sometimes causes psychological dependency and psychosis (e.g. schizophrenia) as a side effect.

On the other hand, Ifenprodil, which is a cerebral circulation improvement drug, shows high affinity to the NR1/NR2B receptor and enhances the morphine-derived analgesic effect. CP-101606, which is a competitive NMDA receptor antagonist, shows selective antagonistic action to the NR1/NR2B receptor and is known to be effective for Parkinson's disease, stroke, migraine, tinnitus, head injury (reference to Patent Document No. 1). These drugs showing high affinity with the NR1/NR2B receptor may highly possibly be analgesics with less side effects on the motor function (e.g. paresthesia), psychosis (e.g. schizophrenia).

Patent Document No. 3 discloses a compound having an analogous structure with that of a piperidine derivative of the present invention and having antagonistic action to NMDA; however, a compound having a hydroxy group as a substituent for $R^3$ of the compound of the present invention is not disclosed. Patent Document Nos. 4 to 6 disclose compounds having analogous structures with that of a piperidine derivative of the present invention; however, there is no practical description of the NMDA receptor antagonistic action.

Patent Document No. 7 discloses a compound having an analogous structure with that of a piperidine derivative of the present invention; however, the selectivity for the subtype of the NMDA receptor is low or the activity is not high.

[Patent Document No. 1] U.S. Pat. No. 5,338,754
[Patent Document No. 2] U.S. Pat. No. 4,232,158
[Patent Document No. 3] WO 96/02250
[Patent Document No. 4] JP 1986-36262 A
[Patent Document No. 5] WO 91/08200
[Patent Document No. 6] UK 881,894
[Patent Document No. 7] WO 03/035641
[Non-patent Document No. 1] NATURE (1976), vol. 263, p. 517
[Non-patent Document No. 2] NATURE (1991), vol. 349, p. 414
[Non-patent Document No. 3] NATURE (1992), vol. 357, p. 70
[Non-patent Document No. 4] NATURE (1992), vol. 358, p. 364
[Non-patent Document No. 5] SCIENCE (1992), vol. 256, p. 1217
[Non-patent Document No. 6] FEBS LETT (1992), vol. 300, p. 39
[Non-patent Document No. 7] STROKE (1997), vol. 28, p. 2244
[Non-patent Document No. 8] TRENDS PHARMA SCI (2001), vol. 22, p. 636
[Non-patent Document No. 9] Journal of Japanese Pharmacological Society (2001), vol. 117, p. 13

DISCLOSURE OF THE INVENTION

Problems to be Solved by the Invention

As described above, NMDA receptor antagonists are expected to be efficacious medicaments for various kinds of central system diseases and cancer pains; however, they have various problems such as low selectivity for receptor subtype, high possibility of causing various side effects because they have non-competitive NMDA receptor antagonistic activity.

Accordingly, it has been desired to develop an antagonist having strong activity and high affinity with preferably subtypes, particularly NR1/NR2B receptor and more preferably scarcely causing any side effects. Specially, development of a clinically useful analgesic for cancer pains has been desired.

Means for Solving the Problems

Based on the results of investigations, inventors of the present invention have found that certain kinds of piperidine derivatives cause strong antagonistic actions for the NR1/NR2B receptor and a remarkable analgesic effect and causes no side effect such as psychotic disturbance and accordingly have completed the following inventions.

The invention provides (1) A Compound of the Formula (I):

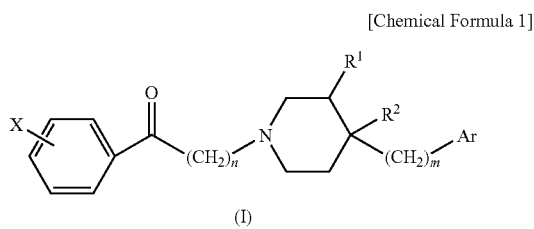

[Chemical Formula 1]

(I)

wherein X is OH or lower alkylsulfonyloxy;
Ar is optionally substituted aryl or optionally substituted heteroaryl;
n is an integer of 1 to 4;
m is an integer of 0 to 1;
$R^1$ is hydrogen;
$R^2$ is OH or
$R^1$ and $R^2$ taken together may form a single bond; excluding that
1) n is 2; m is 0; $R^1$ and $R^2$ taken together may form a single bond; and Ar is optionally substituted phenyl and
2) n is 3; m is 0; $R^1$ and $R^2$ taken together may form a single bond; and Ar is phenyl, a pharmaceutically acceptable salt or a solvate thereof.

(2) The compound described in (1) wherein n is 3 or 4, a pharmaceutically acceptable salt, or a solvated thereof.

(3) The compound described in (1) wherein m is 1, a pharmaceutically acceptable salt or a solvate thereof.

(4) The compound described in (1) wherein n is 3; m is 1; and Ar is optionally substituted phenyl, a pharmaceutically acceptable salt or a solvate thereof.

(5) The compound described in (1) wherein n is 3; m is 1; $R^1$ is hydrogen; $R^2$ is OH; and Ar is optionally substituted phenyl, a pharmaceutically acceptable salt or a solvate thereof.

(6) The compound described in (1) wherein n is 3; m is 1; $R^1$ and $R^2$ taken together may form a single bond; and Ar is optionally substituted phenyl, a pharmaceutically acceptable salt, or a solvate thereof.

(7) The compound described in (1) wherein n is 3; m is 0; $R^1$ and $R^2$ taken together may form a single bond; and Ar is substituted phenyl, a pharmaceutically acceptable salt, or a solvate thereof.

(8) The compound described in (1) wherein Ar is optionally substituted heteroaryl, a pharmaceutically acceptable salt or a solvate thereof.

(9) The compound described in (1) wherein n is 3; m is 0; $R^1$ and $R^2$ taken together may form a single bond; and Ar is optionally substituted heteroaryl, a pharmaceutically acceptable salt or a solvate thereof.

(10) A pharmaceutical composition containing the compound described in any one of (1) to (9).

(11) The pharmaceutical composition described in (10) having NMDA receptor antagonistic activity.

(12) The pharmaceutical composition described in (11) having NR1/NR2B receptor antagonistic activity.

(13) A pharmaceutical composition which contains the compound described in any one of (1) to (9) and which is an analgesic or a medicament for treating migraine, stroke, head injury, Alzheimer's disease, Parkinson's disease, or tinnitus.

(14) A pharmaceutical composition which contains the compound described in any one of (1) to (9) and which is an analgesic.

(15) A method for alleviating pain or treating migraine, stroke, head injury, Alzheimer's disease, Parkinson's disease, or tinnitus comprising administrating the compound described in any one of (1) to (9).

(16) A method for alleviating pain comprising administrating the compound described in any one of (1) to (9).

(17) Use of the compound described in any one of (1) to (9) for manufacturing an analgesic or a medicament for treating migraine, stroke, head injury, Alzheimer's disease, Parkinson's disease, or tinnitus.

(18) Use of the compound described in any one of (1) to (9) for manufacturing an analgesic.

(19) A compound of the formula (I):

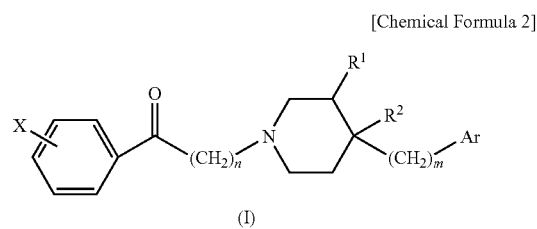

[Chemical Formula 2]

(I)

wherein X is OH or lower alkylsulfonyloxy;
Ar is optionally substituted aryl or optionally substituted heteroaryl;
n is an integer of 1 to 4;
m is an integer of 0 to 1;
$R^1$ is hydrogen;
$R^2$ is OH or
$R^1$ and $R^2$ taken together may form a single bond; excluded that 1) n is 1 or 2; m is 0; $R^1$ and $R^2$ taken together may form a single bond; and Ar is optionally substituted phenyl and
2) n is 3; m is 0; $R^1$ and $R^2$ taken together may form a single bond; and Ar is phenyl, a pharmaceutically acceptable salt or a solvate thereof.

EFFECT OF THE INVENTION

The compound of the present invention may be used not only for treating neuron degeneration such as stroke and brain injury but also for analgesic with less side effects (e.g. an analgesic for cancer pains).

BEST MODES OF THE EMBODIMENTS OF THE INVENTION

The respective groups of the compound (I) is described below.

X is OH, lower alkylsulfonyloxy or lower alkoxy. Lower alkylsulfonyloxy is a group formed by adding lower alkyl as a substituent to a sulfonyloxy group. Examples are $CH_3SO_3$— and $CH_3CH_2SO_3$—. A preferable example is $CH_3SO_3$—. Lower alkyl includes straight chain and branched alkyl groups having 1 to 6 carbon atoms and examples are methyl, ethyl, n-propyl, iso-propyl, n-butyl, iso-butyl, tert-butyl, sec-butyl, n-pentyl, iso-pentyl, neo-pentyl, tert-pentyl, n-pentyl, iso-pentyl, neo-pentyl, tert pentyl and n-hexyl. Preferable examples are alkyl groups having 1 to 3 carbon atoms and particularly preferable examples are methyl or ethyl. Lower alkyl may be substituted with halogen and examples of the substituent groups are $CF_3$—, $CHF_2$—, $CH_2F$—, and $CCl_3$—. Halogen includes F, Cl, and Br. Lower alkyl portion of lower alkoxy is the same as "lower alkyl" described above.

Ar is optionally substituted aryl or optionally substituted heteroaryl. Aryl is phenyl, naphthyl, or a polycyclic aromatic hydrocarbon group (e.g. phenanthryl). Preferably Ar is phenyl. Heteroaryl is a 5 to 6 membered aromatic ring group having 1 to 4 hetero atoms selected from N, O, and S (e.g. furan, thiophene, pyrrole, oxazole, thiazole, imidazole, pyrazole, triazole, pyridine, pyridazine, pyrimidine, pyrazine, and triazine), their condensed rings, or condensed rings of the above-mentioned "aromatic ring" and the above-mentioned "aryl" (e.g. benzothiophene and quinoline). Preferably heteroaryl is thiophene.

The substituent group of the optionally substituted aryl, optionally substituted phenyl or optionally substituted heteroaryl may include OH, halogen (F, Br, and Cl), lower alkyl (e.g. $CH_3$—, $CH_3CH_2$—, and tert-Bu-), lower haloalkyl (e.g. $CF_3$—), lower alkoxy (e.g. $CH_3O$—, $CH_3CH_2O$—, and isopropoxy), lower haloalkoxy (e.g. $CF_3O$— and $CF_3CF_2O$—), lower alkylsulfonyloxy (e.g. $CH_3SO_3$— and $CH_3CH_2SO_3$—), lower haloalkylsulfonyloxy (e.g. $CF_3SO_3$—, $CH_2FSO_3$—, and $CF_3CH_2SO_3$—), arylsulfonyloxy (e.g. $PhSO_3$—), lower alkoxyarylsulfonyloxy (e.g. $CH_3O$-p-$PhSO_3$—), lower alkylarylsulfonyloxy (e.g. $CH_3$-p-$PhSO_3$—), acyloxy (e.g. acetoxy, and propanoyloxy), aroyloxy (e.g. benzoyloxy), acyl (e.g. acetyl), aroyl (e.g. benzoyl), formyl, optionally substituted amino (e.g. amino and dimethylamino), nitro, cyano, lower alkylcarboxy ester (e.g. methoxycarbonyl ester and ethoxycarbonyl ester), carboxy, carbamoyl, optionally substituted aryloxy (e.g. phenoxy, monochlorophenoxy, dichlorophenoxy, and trifluoromethylphenoxy). These substituent groups may be added to 1 to 5 sites, preferably 1 to 2 sites.

The substituent groups for Ar are preferably F, Cl, $CH_3O$—, $CH_3$—, or $CF_3O$—.

The reference character n is an integer of 1 to 6, preferably 1 to 4, and particularly preferably 3.

The reference character m is an integer of 0 or 1 and particularly preferably 1.

$R^1$ is hydrogen, $C_1$ to $C_3$ alkyl (preferably methyl), halogen (F, Cl, Br, I), OH, CN, optionally substituted amino, or optionally substituted alkoxy. The substituent group of optionally substituted amino may be halogen, lower alkyl or acyl. The substituent group of optionally substituted alkoxy may be OH, or halogen (e.g. F, Br, Cl). $R^1$ is preferably H.

$R^2$ is the same as the definition of $R^1$ and preferably OH.

$R^1$ and $R^2$ taken together may form a single bond.

The substituent group needed for exhibiting the activity is OH or lower alkylsulfonyloxy (e.g. $CH_3SO_3$—) for X and preferably OH.

Any compound of the present invention has the NMDA antagonistic action, particularly for the NR1/NR2B receptor, and the following compounds are particularly preferable.

(i) a compound wherein n is 1, 2 or 4;
(ii) a compound wherein m is 1;
(iii) a compound wherein Ar is para-substituted phenyl;
(iv) a compound wherein n is 1 and m is 1;
(v) a compound wherein n is 2 and m is 1;
(vi) a compound wherein n is 3 and m is 1;
(vii) a compound wherein n is 4 and m is 1;
(viii) a compound wherein n is 1 and m is 0;
(ix) a compound wherein n is 2 and m is 0;
(x) a compound wherein n is 4 and m is 0;
(xi) a compound wherein n is 1; m is 1; and Ar is para-substituted phenyl;
(xii) a compound wherein n is 2; m is 1; and Ar is para-substituted phenyl;
(xiii) a compound wherein n is 3; m is 1; and Ar is para-substituted phenyl;
(xiv) a compound wherein n is 4; m is 1; and Ar is para-substituted phenyl;
(xx) a compound wherein n is 1; m is 0; and Ar is para-substituted phenyl;
(xvi) a compound wherein n is 2; m is 0; and Ar is para-substituted phenyl;
(xvii) a compound wherein n is 3; m is 0; and Ar is para-substituted phenyl;
(xviii) a compound wherein n is 4; m is 0; and Ar is para-substituted phenyl;

A typical production method of the compound (I) is exemplified as follows.

[Chemical Formula 3]

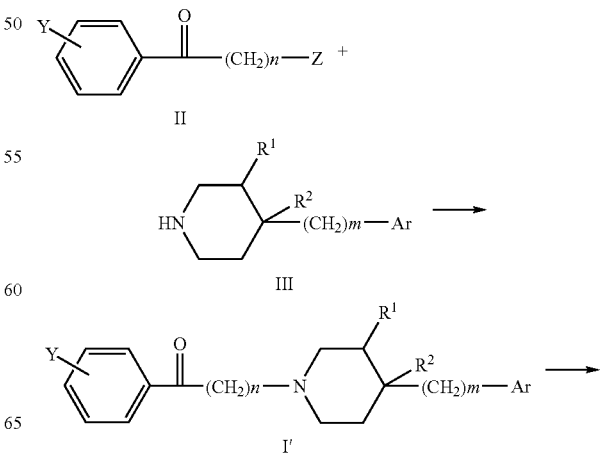

-continued

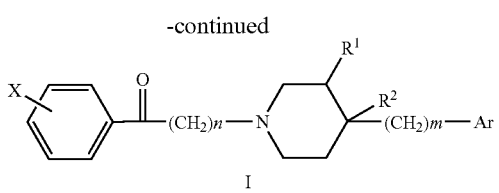

I

The compound (I) includes the compound (I').

In the formula, Y is $CH_3O-$, $CH_3SO_3-$, or 4-methoxybenzenesulfonyloxy: Z is an eliminated group (e.g. halogen such as Cl and Br; sulfonate such as $CH_3SO_3-$ and $CF_3SO_3-$; acyloxy such as $CH_3CO_2-$): other reference characters are the same as defined above: X and Y may be the same (e.g. $CH_3SO_3-$).

The compound (II) is reacted with the compound (III) to obtain the compound (I'), in the presence of a base, if needed. The base to be used may be a carbonate ($K_2CO_3$ and $Na_2CO_3$), NaOH, or a tertiary amine (e.g. $Et_3N$). KBr, NaI, and KI may also be used in combination. A usable solvent is acetonitrile, dimethylformamide (DMF), dimethylsulfoxide (DMSO), tetrahydrofuran (THF), dioxane, methanol, ethanol, pyridine, and diglyme. The reaction temperature is generally about 10 to 200° C. and more preferably about from room temperature to 140° C. and the reaction duration is several hours to several ten hours, preferably about 1 to 20 hours, and more preferably about 3 to 15 hours. The compounds (II) and (III) may be synthesized by conventionally known reaction or commercialized products may be used. In the case Y is $CH_3O-$, the compound (I) wherein X is OH is obtained by heating the compound (I') with hydrochloride, sulfate, or perchlorate of a tertiary amine such as pyridine, methylpyridine, or dimethylpyridine in the presence or absence of a solvent. In the case Y is $CH_3SO_3-$ or 4-methoxybenzenesulfonyloxy, the compound (I) wherein X is OH is obtained by heating the compound (I') with a base such as NaOH, LiOH, KOH, $K_2CO_3$, or $Ca(OH)_2$ in the presence of a solvent such as methanol, ethanol, acetonitrile, DMSO, DMF, or diglyme or absence of the solvent.

If necessary, before the above-mentioned reaction, a proper protection reaction for a functional group may be carried out by a method which is known to a person skilled in the field, and de-protection reaction may be carried out after the reaction.

As a salt of the compound of the present invention, a pharmaceutically acceptable salt may be used, and examples of basicity-adding salts are an alkaline metal salt such as a sodium salt and a potassium salt; an alkaline earth metal salt such as a calcium salt and a magnesium salt; an ammonium salt; a trimethylamine salt, a triethylamine salt; an aliphatic amine salt such as a dicyclohexylamine salt, an ethanolamine salt, a diethanolamine salt, a triethanolamine salt, and a procaine salt; an aralkylamine salt such as N,N-dibenzylethylenediamine; a heterocyclic aromatic amine salt such as a pyridine salt, a picoline salt, a quinoline salt, and an isoquinoline salt; a quaternary ammonium salt such as a tetramethylammonium salt, a tetraethylammonium salt, a benzyltrimethylammonium salt, a benzyltriethylammonium salt, a benzyltributylammonium salt, a methyltrioctylammonium salt, and a tetrabutylammonium salt; and a basic amino acid salt such as an arginine salt and a lysine salt.

Examples of acidity-adding salts are an inorganic acid salt such as a hydrochloride, a sulfate, a nitrate, a phosphate, a carbonate, a hydrogen carbonate, and a perchlorate; an organic acid salt such as an acetate, a propionate, a lactate, a maleate, a fumarate, a tartarate, a malate, a citrate, and an ascorbate; a sulfonic acid salt such as a methanesulfonate, an isethionate, a benzenesulfonate, a p-toluenesulfonate; and an acidic amino acid such as an aspartate and a glutamate.

The compound (I) may be a solvate of water or acetonitrile. The number of hydration of the hydrated compound of the present invention may be fluctuated generally in accordance with a synthetic method, a refining method, or crystallization conditions and it may be in a range of 1 to 5 water molecules per 1 molecule of the compound.

The compound (I) may be converted into a prodrug by a conventional method.

The prodrug is a derivative of the compound of the present invention having a chemically or metabolically decomposable group and is a compound which turns into a pharmaceutically active compound of the present invention in vivo by solvolysis or under a physiological condition. A method for selecting or producing a proper prodrug derivative is described in, for example, Design of Prodrugs, Elsevier, Amsterdam 1985. The prodrug itself may be active.

In the case the compound of the present invention has a hydroxyl group, a prodrug such as an acyloxy derivative and a sulfonyloxy derivative can be obtained by a reaction of the compound having a hydroxyl group and a proper acyl halide, a proper an acid anhydride, a proper sulfonyl chloride, a proper sulfonyl anhydride, and mixed anhydrides, by using a condensation agent, if needed. Examples are $CH_3COO-$, $C_2H_5COO-$, tert-BuCOO-, $C_{15}H_{31}COO-$, PhCOO-, (m-NaOOCPh)COO-, $NaOOCCH_2CH_2COO-$, $CH_3CH(NH_2)COO-$, $CH_2N(CH_3)_2COO-$, $CH_3SO_3-$, $CH_3CH_2SO_3-$, $CF_3SO_3-$, $CH_2FSO_3-$, $CF_3CH_2SO_3-$, $p-CH_3OPhSO_3-$, $PhSO_3-$, and $p-CH_3PhSO_3-$.

The compound (I) can be orally or non-orally administered for animals including human being as a pharmaceutical drug, particularly a preventive or therapeutic drug for various central nervous diseases attributed to the NMDA receptor, specially the NR1/NR2B receptor (e.g. migraine, stroke, cerebral infarction, head injury, Alzheimer's disease, Parkinson's disease, tinnitus, chronic nerve degeneration disease, Huntington's chorea, epilepsy, amyotrophic lateral sclerosis, and nerve degeneration relevant to bacteria and virus infection), or an analgesic (for cancer pains). Examples of the administration formulation may include a granule, a tablet, a capsule, and an injection. For the formulation, various kinds of additives, e.g. an excipient, a disintegrator, a binder, a lubricant, a stabilizer, a coloring agent, and a coating agent may be used. The administration dose differs depending on the age, the body weight and the symptoms of an examinee, and administration method and is not particularly limited; however, in the case of oral administration, about 1 mg to 5,000 mg for an adult per a day and in the case of non-oral administration, about 0.1 mg to 1,000 mg.

EXAMPLES

The present invention is further explained by the following Examples, which are not intended to limit the scope of the present invention.

Example 1

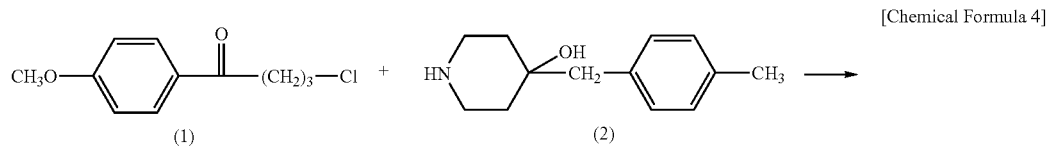

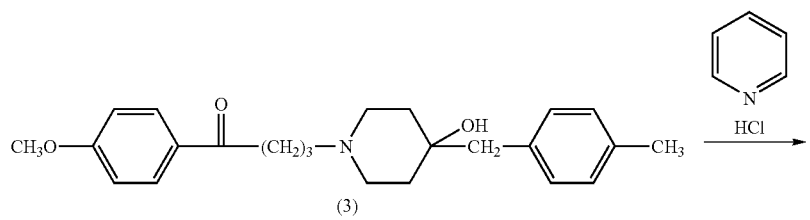

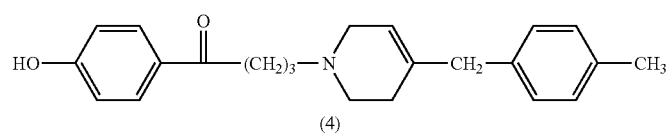

Synthesis of 4-[4-Hydroxy-4-(4-methyl-benzyl)-piperidin-1-yl]-1-(4-methoxy-phenyl)-butan-1-one (3)

A mixture of 1.62 g of 4-chloro-1-(4-methoxy-phenyl)-butan-1-one (1), 1.20 g of 4-(4-methyl-benzyl)-piperidin-4-ol (2), 1.62 g of $K_2CO_3$, and 0.49 g of KI in acetonitrile (30 mL) was stirred and refluxed at 105 to 110° C. for 9 hours under nitrogen atmosphere. After the solvent was removed, ice water was added and the mixture was extracted with ethyl acetate. The organic layer was successively washed with water and brine and dried over $MgSO_4$. After the solvent was removed, the obtained oily residue was purified by silica gel chromatography (chloroform:methanol=20/1 to 10/1) and the purified product was recrystallized from $AcOEt/Et_2O$ to afford 1.73 g of compound (3).

NMR ($CDCl_3$) δ ppm (300 MHz) (Free) 1.45-1.75 (4H, m), 1.936 (2H, quint, J=7.2 Hz), 2.24-2.76 (4H, m), 2.324 (3H, s), 2.427 (2H, t, J=6.9 Hz), 2.692 (2H, s), 2.935 (2H, t, J=7.2 Hz), 3.865 (3H, s) 6.922 (2H, d, J=9.0 Hz), 7.04-7.16 (4H, m), 7.945 (2H,d, J=9.0 Hz) Elemental analysis (%): C24H31NO.1/5H2O Calculated value: C=74.85, H=8.22, N=3.64, Experimental value: C=74.84, H=8.23, N=3.85, Synthesis of 1-(4-Hydroxy-phenyl)-4-[4-(4-methyl-benzyl)-3,6-dihydro-2H-pyridin-1-yl]-butan-1-one (4)

A mixture of 1.40 g of compound (3) and 7.29 g of pyridine hydrochloride was stirred at 180 to 185° C. for 6.5 hours. After cooled to room temperature, the mixture was made basic with aqueous $NaHCO_3$ and then extracted with ethyl acetate. The organic layer was successively washed with water and brine and dried over $MgSO_4$. After the solvent was removed, the obtained oily residue was purified by silica gel chromatography (chloroform:methanol=50/1 to 20/1) to obtain 0.34 g of the oily compound (4). Thus-obtained free compound was crystallized in form of an oxalate and recrystallized from $MeOH/Et_2O$.

(4)

NMR ($CDCl_3$) δ ppm (300 MHz) (Free) 1.987 (2H, quint, J=7.5 Hz) 1.95-2.15 (2H, m), 2.290 (3H, s), 2.612 (2H,t, J=7.8 Hz), 2.681 (2H, t, J=6 Hz), 2.899 (2H, t, J=7.2 Hz), 3.114 (2H, brs), 3.238 (2H, s), 5.407 (1H, brs), 6.560 (2H, d, J=8.7 Hz), 6.96-7.10 (4H, m), 7.648 (2H, d, J=8.7 Hz).

Elemental analysis (%): C23H27NO2.C2H2O4.1/10H2O
Calculated: C=68.04, H=6.67, N=3.17,
Found: C=67.94, H=6.65, N=3.41,

Example 2

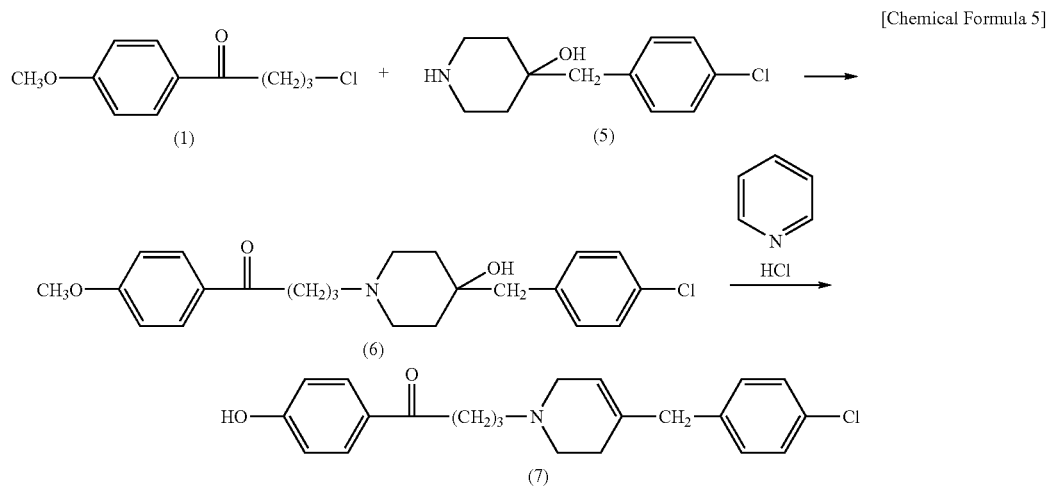

Synthesis of 4-[4-(4-Chloro-benzyl)-4-hydroxy-piperidin-1-yl]-1-(4-methoxy-phenyl)-butan-1-one (6)

A mixture of 2.11 g of 4-chloro-1-(4-methoxy-phenyl)-butan-1-one (1), 1.60 g of 4-(4-chloro-benzyl)-piperidin-4-ol (5), 1.96 g of $K_2CO_3$, and 0.45 g of KI in acetonitrile (50 mL) was stirred and refluxed at 100 to 110° C. for 19 hours under nitrogen atmosphere. After the solvent was removed, ice water was added and the mixture was extracted with ethyl acetate. The organic layer was successively washed with water and brine and dried over $MgSO_4$. After the solvent was removed, the obtained oily residue was purified by silica gel chromatography (chloroform:methanol=20/1 to 10/1) and the purified product was recrystallized from AcOEt/Et2O to afford 1.55 g of compound (6).

Elemental analysis (%): C23H28ClNO3.1/3H2O
Calculated: C=67.72, H=7.08, N=3.43,
Found: C=67.67, H=6.91, N=3.51, Synthesis of [4-(4-chloro-benzyl)-3,6-dihydro-2H-pyridin-1-yl]-1-(4-hydroxy-phenyl)-butan-1-one (7)

A mixture of 1.25 g of compound (6) and 4.31 g of pyridine hydrochloride was stirred at 180 to 185° C. for 5 hours. After cooled to room temperature, the mixture was made basic with aqueous $NaHCO_3$ and then extracted with ethyl acetate. The organic layer was successively washed with water and brine and dried over $MgSO_4$. After the solvent was removed, the obtained oily residue was purified by silica gel chromatography (chloroform:methanol=50/1 to 20/1) to afford 0.55 g of the oily compound (7). The free compound (7) was crystallized in form of an oxalate and recrystallized from MeOH/i-PrOH.

(7)
NMR (CDCl3) δ ppm (300 MHz) (Free) 1.985 (2H, quint, J=7.2 Hz), 2.00-2.16 (2H, m), 2.598 (2H, t, J=7.5 Hz), 2.668 (2H, t, J=5.7 Hz), 2.902 (2H, t, J=7.2 Hz), 3.100 (2H, brs), 3.234 (2H,brs) 5.414 (1H,brs), 6.563 (2H, d, J=8.7 Hz), 7.041 (2H, d, J=8.4 Hz), 7.177 (2H, d, J=8.4 Hz), 7.665 (2H, d, J=8.7 Hz),
Elemental analysis (%): C22H24ClNO2.C2H2O4
Calculated: C=62.68, H=5.70, Cl=7.71, N=3.05,
Found: C=63.01, H=5.77, Cl=7.52, N=3.41, The following compounds (9), (10), and (11) were synthesized as described above.

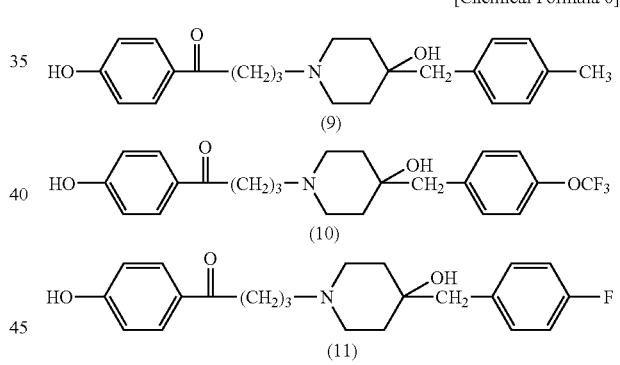

(9)
NMR (CDCl3) δ ppm (300 MHz) (Free) 1.46-1.61 (2H, m), 1.806 (2H, t-d J1=13.5 Hz, J2=3.6 Hz), 1.972 (2H, quint, J=7.2 Hz), 2.318 (2H,s), 2.38-2.52 (2H,m), 2.566 (2H, t, J=7.2 Hz), 2.700 (2H, s), 2.78-2.90 (2H, m) 2.875 (2H, t, J=7.2 Hz), 6.575 (2H, d, J=8.7 Hz), 7.050 (2H, d, J=8.1 Hz), 7.110 (2H,d, J=8.1 Hz), 7.671 (2H,d, J=8.7 Hz)
Elemental analysis (%): C23H29NO3.1/2C2H2O4.1/4H2O
Calculated: C=68.21, H=7.59, N=3.46,
Found: C=68.14, H=7.41, N=3.40,

(10)
NMR (CDCl3) δ ppm (300 MHz) (Free) 1.50-1.60 (2H, m), 1.738 (2H, t-d J1=13.8 Hz, J2=3.9 Hz), 1.957 (2H, quint, J=6.9 Hz), 2.40-2.86 (2H, m), 2.765 (2H, s), 2.956 (2H,t, J=6.9 Hz), 6.858 (2H, d, J=8.7 Hz), 7.143 (2H,d, J=8.14z), 7.251 (2H,d, J=8.7 Hz), 7.863 (2H,d, J=8.4 Hz)
Elemental analysis (%): C23H26F3NO4.1/4H2O
Calculated: C=62.51, H=6.04, N=3.17, F=12.90,
Found: C=62.32, H=6.03, N=3.26, F=13.32, (11)

NMR (CDCl$_3$) δ ppm (300 MHz) (Free) 1.64-2.26 (6H, m), 2.811 (2H,s), 3.00-3.44 (8H,m), 6.868 (2H, d, J=8.7 Hz), 6.94-7.26 (4H,m), 7.868 (2H, d, J=8.7 Hz)

Example 3

[Chemical Formula 7]

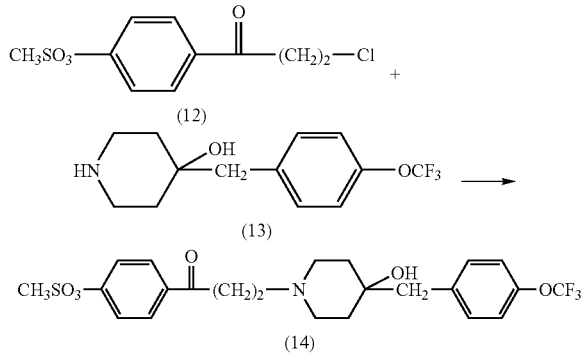

Synthesis of Methanesulfonic acid 4-{3-[4-hydroxy-4-(4-trifluoromethoxy-benzyl)-piperidin-1-yl]-propionyl}-phenyl ester (14)

A mixture of 0.54 g of methanesulfonic acid 4-(4-chlorobutyryl)-phenyl ester (12), 0.45 g of compound (13), 0.45 g of K$_2$CO$_3$, and 0.14 g of KI in acetonitrile (20 mL) was stirred and refluxed at 105 to 110° C. for 9.5 hours under nitrogen atmosphere. After the solvent was removed, ice water was added and the mixture was extracted with ethyl acetate. The organic layer was successively washed with water and brine and dried over MgSO$_4$. After the solvent was removed, the obtained oily residue was purified by silica gel chromatography (chloroform:methanol=10/1) to afford 0.21 g of the oily compound (14). The free compound (14) was crystallized in form of an oxalate and recrystallized from MeOH/i-PrOH-Et$_2$O.

(14)

NMR (CDCl$_3$) δ ppm (300 MHz) (Free) 1.42-1.56 (2H, m), 1.637 (2H, t-d J1=13.8 Hz, J2=4.5 Hz), 1.967 (2H, quint, J=7.2 Hz), 2.320 (2H, t-d J1=11.4 Hz, J2=2.4 Hz), 2.448 (2H, t, J=7.2 Hz), 2.60-2.74 (2H, m), 2.719 (2H, s), 2.978 (2H, t, J=7.2 Hz), 3.197 (3H, s), 7.139 (2H, d, J=9.0 Hz), 7.213 (2H, d, J=8.7 Hz), 7.368 (2H, d, J=9.0 Hz), 8.029 (2H, d, J=8.7 Hz)

Elemental analysis (%): C24H28F3NO6S.C2H2O4
Calculated: C=51.57, H=4.99, N=2.31, F=9.41, S=5.30,
Found: C=51.88, H=5.00, N=2.54, F=9.47, S=5.68, The following compounds (15), (16), and (17) were synthesized as described above.

[Chemical Formula 8]

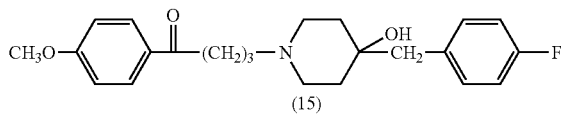

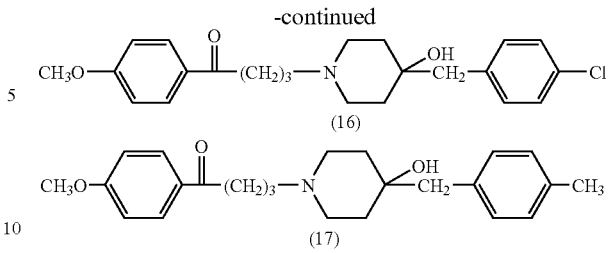

(15)

Elemental analysis (%): C23H25ClF3NO3.C2H2O4
Calculated: C=63.15, H=6.36, F=4.00, N=2.95,
Found: C=64.16, H=6.52, F=3.64, N=3.09, (16)

Elemental analysis (%): C23H28ClNO3.1/3H2O
Calculated: C=67.72, H=7.08, Cl=8.69, N=3.43,
Found: C=67.67, H=6.91, Cl=9.38, N=3.51, (17)

NMR (CDCl$_3$) δ ppm (300 MHz) (Free) 1.45-1.75 (4H, m), 1.936 (2H, quint, J=7.2 Hz), 2.24-2.76 (4H, m), 2.324 (3H, s) 2.427 (2H, t, J=6.9 Hz), 2.692 (2H, s), 2.935 (2H, t, J=7.2 Hz), 3.865 (3H, s) 6.922 (2H, d, J=9.0 Hz), 7.04-7.16 (4H, m), 7.945 (2H, d, J=9.0 Hz)

Elemental analysis (%): C24H31NO.1/5H2O
Calculated: C=74.85, H=8.22, N=3.64,
Found: C=74.84, H=8.23, N=3.85, The following compounds (18), (19), and (20) were synthesized as described above.

[Chemical Formula 9]

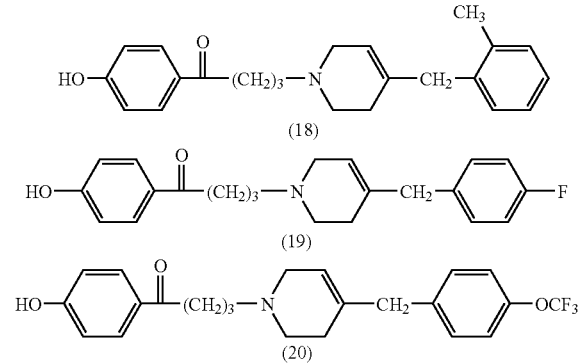

(18)

NMR (CDCl$_3$) δ ppm (300 MHz) (Free) 1.980 (2H, quint, J=6.9 Hz), 2.00-2.20 (2H, m), 2.203 (3H,s), 2.603 (2H, t, J=7.5 Hz), 2.705 (2H, t, J=5.7 Hz), 2.890 (2H, t, J=6.9 Hz), 3.067 (2H, brs), 3.247 (2H,brs) 5.180 (2H,brs), 6.557 (2H, d, J=8.7 Hz), 6.50-6.90 (1H,m), 7.02-7.14 (4H,m) 7.646 (2H, d, J=9.0 Hz)

Elemental analysis (%): C23H27NO2.3/5C2H2O4
Calculated: C=72.04, H=7.04, N=3.47,
Found: C=72.12, H=7.25, N=3.67, (19)

NMR (CDCl$_3$) δ ppm (300 MHz) (Free) 1.989 (2H, quint, J=7.2 Hz), 2.00-2.15 (2H, m), 2.606 (2H, t, J=7.5 Hz), 2.680 (2H, t, J=6.0 Hz), 2.901 (2H, t, J=7.2 Hz), 3.113 (2H, brs), 3.237 (2H,brs) 5.406 (1H, brs), 6.569 (2H, d, J=8.4 Hz), 6.85-7.12 (4H, m), 7.664 (2H, d, J=8.4 Hz)

Elemental analysis (%): C22H24FNO2.1/2C2H2O4.4/3H2O
Calculated: C=65.70, H=6.15, N=3.33, F=4.52,
Found: C=65.72, H=5.84, N=3.38, F=4.25, (20)

NMR (CDCl$_3$) δ ppm (300 MHz) (Free) 1.88-2.16 (4H, m), 2.505 (2H, t, J=6.0 Hz), 2.55-2.70 (2H,m) 2.945 (2H, t, J=6.6 Hz), 3.039 (2H, brs), 5.400 (1H,brs), 6.841 (2H, d, J=7.2 Hz), 7.08-7.28 (4H, m) 7.851 (2H, d, J=7.2 Hz), Elemental analysis (%): C23H24F3NO3.C2H2O4.1/10H2O
Calculated: C=58.73, H=5.17, F=11.15, N=2.74,
Found: C=58.50, H=5.00, F=11.02, N=2.94, Example 4

(24). A mixture of 0.35 g of compound (24) in trifluoroacetic acid (10 mL) was refluxed for 4 hours. After the excess trifluoroacetic acid was removed, the residue was made basic with aqueous Na$_2$CO$_3$.

The precipitated roughly produced crystal was purified by silica gel chromatography (chloroform:methanol=20/1 to 10/1) to afford 0.25 g of a crystal of compound (25).

(25)

NMR (DMSO-d6) δ ppm (300 MHz) (Free) 1.813 (2H, quint, J=7.5 Hz), 2.36-2.48 (4H, m), 2.592 (2H, t, J=5.7 Hz), 2.941 (2H, t, J=7.2 Hz), 3.038 (2H, brs), 3.741 (3H, s), 6.018 (1H, brs), 6.833 (2H, d, J=8.7 Hz), 6.882 (2H, d, J=8.7 Hz), 7.344 (2H, d, J=8.7 Hz), 7.844 (2H, d, J=8.7 Hz)

Elemental analysis (%): C22H25NO3.H2O
Calculated value: C=71.52, H=7.37, N=3.79,
Experimental value: C=71.23, H=7.40, N=3.97,

[Chemical Formula 10]

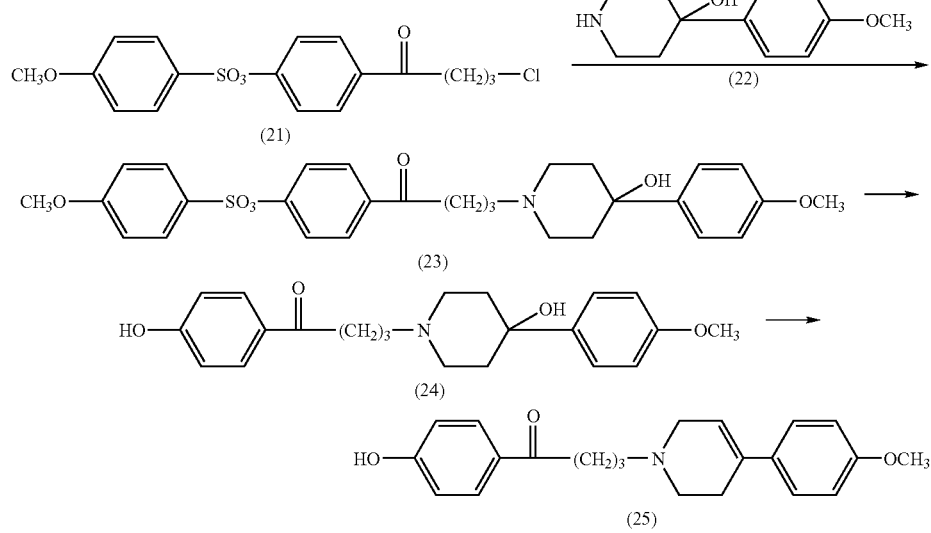

Synthesis of 1-(4-Hydroxy-phenyl)-4-[4-(4-methoxy-phenyl)-3,6-dihydro-2H-pyridin-1-yl]-butan-1-one (25)

A mixture of 2.58 g of 4-methoxy-benzenesulfonic acid 4-(4-chloro-butyryl)-phenyl ester (21), 1.30 g of 4-(4-methoxy-phenyl)-piperidin-4-ol (22), 1.74 g of K$_2$CO$_3$, and 0.52 g of KI in acetonitrile (50 mL) was stirred and refluxed at 105 to 110° C. for 10 hours under nitrogen atmosphere. After the solvent was removed, ice water was added and the mixture was extracted with ethyl acetate. The organic layer was successively washed with water and brine and dried over MgSO$_4$. After the solvent was removed, the obtained oily residue was purified by silica gel chromatography (ethyl acetate:methanol=10/1) and recrystallized from AcOEt/Et$_2$O to afford 1.34 g of compound (23). To 1.20 g of compound (23) were added 1.95 mL of 4N—NaOH and 15 mL of DMSO, and the mixture was stirred at 55° C. for 2.5 hours. After being cooled, the mixture was made acidic with 2N—HCl and turned to be alkaline with aqueous NaHCO$_3$ and then the mixture was extracted with ethyl acetate. The organic layer was successively washed with water and brine and dried over MgSO$_4$. After the solvent was removed, the obtained oily residue was purified by silica gel chromatography (chloroform:methanol=5/1 to 3/1) and crystallized to afford 0.55 g of compound The following compounds (26) to (32) were synthesized as described above.

[Chemical Formula 11]

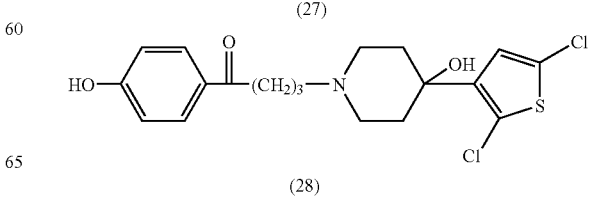

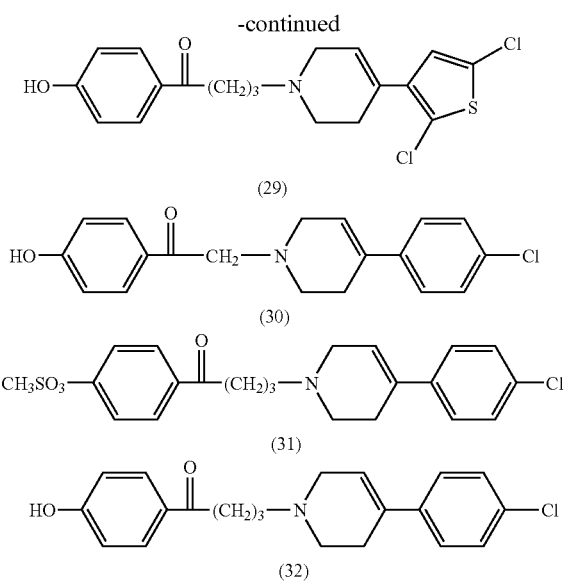

(26)

NMR (CDCl$_3$) δ ppm (300 MHz) (Free) 2.065 (2H, quint, J=6.9 Hz), 2.50-2.60 (2H, m), 2.604 (2H, t, J=7.5 Hz), 2.763 (2H, t, J=5.7 Hz) 3.069 (2H, t, J=6.9 Hz), 3.15-3.25 (2H, m), 3.162 (3H, s), 3.806 (3H, S), 5.942 (1H, brs), 6.854 (2H, d, J=8.7 Hz), 7.25-7.40 (4H, m), 8.046 (2H, d, J=8.7 Hz)

(27)

NMR (CDCl$_3$) δ ppm (300 MHz) (Free) 1.76-1.88 (2H, m), 1.986 (2H, quint, J=6.9 Hz), 2.131 (2H, t-d, J1=13.2 Hz, J2=4.2 Hz), 2.36-2.50 (2H, m), 2.469 (2H, t, J=6.9 Hz), 2.66-2.80 (2H, m), 2.995 (2H, t, J=6.9 Hz), 3.190 (3H s), 6809 (1H, s), 7.373 (2H, d, J=8.7 Hz), 8.046 (2H, d, J=8.7 Hz)

(28)

NMR (DMSO-d6) δ ppm (300 MHz) (Free) 1.58-1.72(2H, m), 1792 (2H, quint, J=6.6 Hz), 2.00-2.75 (8H, m), 2.902 (2H, t, J=6.9 Hz), 5.250 (1H, s), 6.838 (2H, d, J=8.7 Hz), 7.052(1H, s), 7.848 (2H, d, J=8.7 Hz), (29)

NMR (CDCl$_3$) δ ppm (300 MHz) (Free) 2.018 (2H, quint, J=7.2 Hz), 2.36-2.46 (2H, m), 2.533 (2H, t, J=6.9 Hz), 2.653 (2H, t, J=5.7 Hz), 3.033 (2H, t, J=7.2 Hz), 3.08-3.16 (2H, m), 3.179 (3H, s), 5.973 (1H, brs), 6.688 (1H, s), 7.364 (2H, d, J=8.7 Hz), 8.045 (2H, d, J=8.7 Hz)

(30)

NMR (DMSO-d6) δ ppm 2.41-2.46 (m, 2H), 2.75 (t, J=5.6 Hz, 2H), 3.16-3.24 (m, 2H), 3.83 (s, 2H), 4.07 (brs, 1H), 6.17-6.19 (m, 1H), 6.83 (d, J=8.4 Hz, 2H), 7.37 (d, J=8.4 Hz, 2H), 7.43 (d, J=8.4 Hz, 2H), 7.88 (d, J=8.4 Hz, 2H).

mp 206-208° C. (decomp)

(31)

NMR (CDCl$_3$/TMS) δ ppm 2.03 (quint, J=6.8 Hz, 2H), 2.44-2.49 (m, 2H), 2.54 (t, J=6.8 Hz, 2H), 2.69 (t, J=6.0 Hz, 2H), 3.03 (t, J=6.8 Hz, 2H), 3.11-3.15 (m, 2H), 3.17 (s, 3H), 6.02-6.04 (m, 1H), 7.27-7.29 (m, 4H), 7.35 (d, J=8.8 Hz, 2H), 8.03 (d, J=8.8 Hz, 2H).

mp 122-125° C. (decomp)

(32)

NMR (CDCl$_3$/TMS) δ ppm 1.81 (quint, J=7.2 Hz, 2H), 2.40-2.45 (m, 2H), 2.60 (t, J=7.2 Hz, 2H), 2.94 (t, J=7.2 Hz, 2H), 3.03-3.07 (m, 2H), 3.17 (d, J=4.0 Hz, 2H), 4.08(brs, 1H), 6.17-6.19 (m, 1H), 6.83 (d, J=8.8 Hz, 2H), 7.37 (d, J=8.8 Hz, 2H), 7.43 (d, J=8.8 Hz, 2H), 7.83 (d, J=8.8 Hz, 2H).

mp 197-199° C. (decomp)

Experiment Example 1

Experiment of Binding to NMDA Receptor

Competitive binding assays of the test compounds (10, 18 and 19) were carried out using Ifenprodil, which is an antagonist specific for the NR1/NR2B subtype receptor, as a ligand.

Male Slc: Wistar rats were killed by beheading, the brains were picked out and the cerebral cortex was fractionated. The cerebral cortex was homogenized with ice-cooled 50 mM Tris-HCl buffer (pH 7.4) in an amount 20 times of the cerebral cortex and centrifuged at 4° C. and 27,500×g for 10 minutes. The obtained precipitate was suspended with the same buffer solution and again centrifuged. These steps were repeated three times and the obtained precipitate was suspended with the buffer solution and stored at −80° C. Immediately before the experiment, the stored suspension was thawed at room temperature and centrifuged at 4° C. and 27,500×g for 10 minutes and the obtained precipitate was suspended with the buffer solution. Further the resulting solution was diluted 10 times with the buffer solution and the obtained solution was used as a membrane preparation for the experiment.

For the binding experiment, 10 μL of test compounds with different concentrations, 10 μL of [$^3$H]-Ifenprodil, and 10 μL GBR-12909 were added to 470 μL of the above-mentioned membrane preparation and incubated at icing temperature for 120 minutes. The final concentration of [$^3$H]-Ifenprodil was adjusted to be 5 nM and the final concentration of GBR-12909 was adjusted to be 3 μM. DMSO, which is a solvent, was used for measurement of the total binding quantity and 100 μM of Ifenprodil was used for measurement of the non-specific binding quantity. In this connection, GBR-12909 was added to block the binding of [$^3$H]-Ifenprodil to the non-polyamine-sensitive site. After the incubation, the bounded bodies and the free bodies were separated by Whatman GF/C filter paper (Whatman Inc.) and the filter paper was washed four times with 2.5 mL of the ice-cooled buffer solution. The filter paper was immersed in a liquid scintillation (Clear-Sol I, Nacalai Tesque Co., Ltd.) in a vial and the radioactivity (dpm) was measured by a liquid scintillation counter. The binding inhibition ratio (%) was calculated from the measured values according to the following equation and the dose for inhibiting 50% binding (IC$_{50}$) was calculated. The IC$_{50}$ values of the test compounds are shown in Table 1. As a comparative agent, (±)CP-101606, an NR1/NR2B receptor antagonist was used.

Formulas of GBR-12909 (vanoxerine) and CP-101606 are shown in Chemical Formula 11.

[Chemical Formula 12]

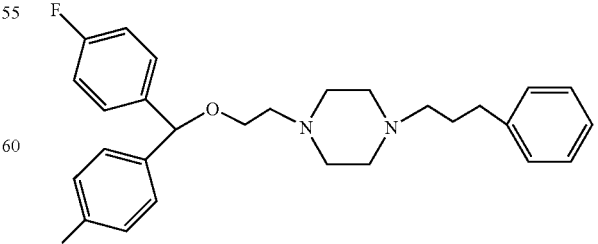

2HCl
GBR-12909

-continued

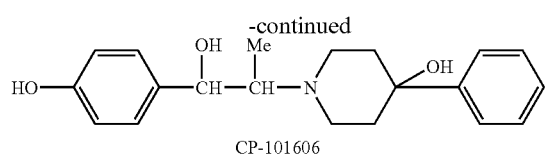

CP-101606

Binding inhibition ratio (%)=100−[(binding quantity in the presence of the test compound−non-specific binding quantity)/(total binding quantity−non-specific binding quantity)]×100

The results of the NR1/NR2B receptor binding experiment are shown in Table 1.

TABLE 1

| Compound No. | IC$_{50}$ (μM) |
|---|---|
| 10 | 0.016 |
| 18 | 0.004 |
| 19 | 0.002 |
| 32 | 0.003 |
| CP-101606 | 0.016 |

From the shown results, it is made clear that the compounds of the present invention show strong binding property to the NR1/NR2B receptor.

Experiment Example 2

Experiment of Binding to PCP Receptor

MK-801 is reported to bind to PCP receptor and cause psychosis. Therefore, competitive binding assays using MK-801 of the test compounds (10, 18 and 19) with CP-101606, an NR1/NR2B receptor antagonist, were carried out.

Male Slc: Wistar rats were used and after beheading of the rats, the brains were picked out and the cerebral cortex was fractionated. The cerebral cortex was homogenized with ice-cooled 5 mM Tris-HCl buffer (pH 7.8) in an amount 20 times as much and centrifuged at 4° C. and 27,500×g for 10 minutes. The obtained precipitate was suspended with the same buffer solution and again centrifuged. These steps were repeated three times and the obtained precipitate was suspended with the buffer solution and stored at −80° C. Immediately before the experiment, the stored suspension was thawed at room temperature and centrifuged at 4° C. and 27,500×g for 10 minutes and the obtained precipitate was suspended with the buffer solution. Further the resulting solution was diluted 2.5 times with the buffer solution and the obtained solution was used as a membrane preparation for the experiment.

For the binding experiment, 10 μL of test compounds with different concentrations and 10 μL of marked ligand [$^3$H] MK-801 were added to 480 μL of the above-mentioned membrane preparation sample and incubated at 25° C. for 60 minutes. The final concentration of [$^3$H] MK-801 was adjusted to be 2 nM. DMSO, which is a solvent, was used for measurement of the total binding quantity and 10 μM of (+)MK-801 was used for measurement of the non-specific binding quantity. After the incubation, the bonded bodies and the free bodies were separated by Whatman GF/C filter paper (manufactured by Whatman Inc.) and the filter paper was washed four times with 2.5 mL of the ice-cooled buffer solution. The filter paper was immersed in a liquid scintillation in a vial (Clear-Sol I, manufactured by Nacalai Tesque Co., Ltd.) and the radiation dose (dpm) was measured by a liquid scintillation counter. The binding inhibition ratio (%) was calculated from the measured values according to the following equation and the dose for inhibiting 50% binding (IC$_{50}$) was calculated. The IC$_{50}$ values of the test compounds are shown in Table 2.

The formula of MK-801 (diazocilpine maleate) is shown as follows.

[Chemical Formula 13]

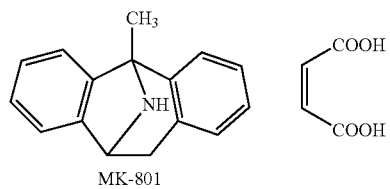

MK-801

Binding inhibition ratio (%)=100−[(binding quantity in the presence of the test compound−non-specific binding quantity)/(total binding quantity−non-specific binding quantity)]×100

The results of the PCP receptor binding experiment are shown in Table 2.

TABLE 2

| Compound No. | IC$_{50}$ (μM) |
|---|---|
| 10 | 20 |
| 18 | 3 |
| 19 | 10 |
| CP-101606 | 13 |

From the shown results, it is made clear that IC$_{50}$ values in the case of using the compounds (10, 18 and 19) of the present invention for the PCP receptor are similar to that of CP-101606 and the compounds are not competitive with MK-801. Accordingly, the compounds of the present invention are supposed to cause no side effect of psychosis or the like.

Experimental Example 3

Expression and Electric Physiological Experiment of NMDA Receptor

Messenger RNA (mRNA) was transcribed with complementary DNA (cDNA) of mouse NMDA receptor subunits and the mRNA was injected in oocytes of Xenopus Laevis. From two days after the injection, the inward current induced by NMDA was recorded by two electrode membrane potential fixation apparatus. The injection amount of the mRNA was 0.6/0.6 ng on the basis of NR1/NR2B per one oocyte to co-expression of the subunits. Solutions of the test compound (18) with different concentrations were added to the oocytes and the inward current induced by NMDA was recorded by two electrode membrane potential fixation apparatus. The extercellular solution was Mg$^{2+}$-free ND96 (NaCl 96 mM, KCl 2 mM, CaCl$_2$ 1.8 mM, and Hepes 5 mM and pH=7.5) and the potential was retained at −60 mV. The NMDA current was induced by using NMDA 100 μM and glycine 10 μM. The measured values of the recorded inward current induced by NMDA were substituted in the following equation to calculate the electric response % and the dose for inhibiting 50% (IC$_{50}$) were calculated. The IC$_{50}$ values for the respective NR1/NR2A, C, and D receptors were calculated.

Electric response (%)=(inward current induced by NMDA in the presence of the test compound/inward current induced by NMDA in the absence of the test compound)×100

Generally, if the test compound shows the antagonistic effect for the NMDA receptor, Calcium influx to the nerve cells is decreased and the electric response % is deteriorated.

The results of the $IC_{50}$ values of the test compound (18) for the subfamilies of NR1/NR2 receptor are shown in Table 3.

TABLE 3

| Compound No. | $IC_{50}(\mu M)$ | | | |
| --- | --- | --- | --- | --- |
| | NR1/NR2A | NR1/NR2B | NR1/NR2C | NR1/NR2D |
| 18 | >30 | 4.6 | >30 | >30 |

From the above-mentioned results, the test compound (18) is made clear to have specific antagonistic effect on the NR1/NR2B receptor.

Experimental Example 4

Analgesic Effect in Mouse Formalin Test

The pain behavior attributed to formalin can be classified into two time-dependent phases and mice show pain behaviors, so-called licking and biting. In the first phase, acute pain was caused within 5 minutes immediately after formalin administration, and in the second phase, inflammatory pain was caused for 20 minutes from 10 to 30 minutes after the administration. ICR type male mice (5-week old) were used for the experiment. Formalin (2%) was subcutaneously injected to the right hind paw of the mice. The test compound (18) was dissolved in a solution, DMSO:HCO50:saline=1.5:1:7.5 and injected in difference concentrations into the vein 5 minutes before the formalin administration. The pain behavior time was measured for 30 minutes after formalin administration. The pain behavior time is to be shortened in the case the test compound causes analgesic effect. The measured time is substituted in the following equation to calculate the analgesic ratio (%) and the dose for 50% efficacy ($ED_{50}$) was calculated. $ED_{50}$ of the test compound in the first phase and the second phase is shown in Table 4.

Analgesic ratio (%)=(pain behavior time in the presence of the test compound/pain behavior time in the absence of the test compound)×100

TABLE 4

| Compound No. | ($ED_{50}$, mg/kg) | |
| --- | --- | --- |
| | The first phase | The second phase |
| 18 | 1.1 | 0.7 |

The analgesic effect of the test compound (18) was confirmed.

The above-mentioned results show the compound of the present invention has good activity as an analgesic in vivo.

The compounds of the present invention other than the exemplified compounds also show the same or higher antagonistic activity for the NR1/NR2B receptor.

INDUSTRIAL APPLICABILITY OF THE INVENTION

The present invention gives a compound showing specific antagonistic effect on a glutamate receptor of central nervous cells, particularly on NR1/NR2B receptor, which is one of NMDA receptor, and useful as analgesic or a nerve protection drug with less side effect for motor function (paresthesia) and psychosis (schizophrenia).

The invention claimed is:

1. A compound of the formula (I):

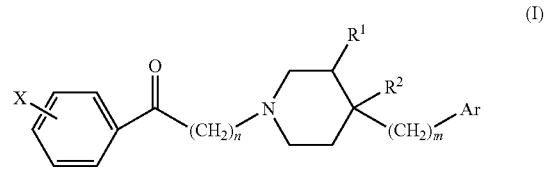

wherein X is OH or lower alkylsufonyloxy;
Ar is optionally substituted aryl or optionally substituted heteroaryl;
n is an integer of 1 to 4;
m is an integer of 0 to 1;
$R^1$ is hydrogen;
$R^2$ is OH or
$R^1$ and $R^2$ taken together may form a single bond;
excluding that
1) n is 2; m is 0; $R^1$ and $R^2$ taken together may form a single bond; and Ar is optionally substituted phenyl and
2) n is 3; m is 0; $R^1$ and $R^2$ taken together may form a single bond; and Ar is phenyl,
or a pharmaceutically acceptable salt or a hydrate thereof.

2. A compound according to claim 1 wherein n is 3 or 4, or a pharmaceutically acceptable salt, or a hydrate thereof.

3. A compound according to claim 1 wherein m is 1, or a pharmaceutically acceptable salt or a hydrate thereof.

4. A compound according to claim 1 wherein n is 3; m is 1; and Ar is optionally substituted phenyl, or a pharmaceutically acceptable salt or a hydrate thereof.

5. A compound according to claim 1 wherein n is 3; m is 1; $R^1$ is hydrogen; $R^2$ is OH; and Ar is optionally substituted phenyl, or a pharmaceutically acceptable salt or a hydrate thereof.

6. A compound according to claim 1 wherein n is 3; m is 1; $R^1$ and $R^2$ taken together may form a single bond; and Ar is optionally substituted phenyl, or a pharmaceutically acceptable salt, or a hydrate thereof.

7. A compound according to claim 1 wherein n is 3; m is 0; $R^1$ and $R^2$ taken together may form a single bond; and Ar is substituted phenyl, or a pharmaceutically acceptable salt, or a hydrate thereof.

8. A compound according to claim 1 wherein Ar is optionally substituted heteroaryl, or a pharmaceutically acceptable salt or a hydrate thereof.

9. A compound according to claim 1 wherein n is 3; m is 0; $R^1$ and $R^2$ taken together may form a single bond; and Ar is optionally substituted heteroaryl, or a pharmaceutically acceptable salt or a hydrate thereof.

10. A pharmaceutical composition comprising a compound according to claim 1 and at least one pharmaceutically acceptable carrier.

11. The pharmaceutical composition according to claim 10 having NMDA receptor antagonistic activity.

12. The pharmaceutical composition according to claim 11 having NR1/NR2B receptor antagonistic activity.

13. A pharmaceutical composition comprising a compound according to claim 1 which is a medicament for treating migraine.

14. A pharmaceutical composition comprising a compound according to claim 1 which is an analgesic.

15. A method for treating migraine, comprising administrating a compound according to claim 1.

16. A method for alleviating pain comprising administrating a compound according to claim 1.

17. A method for manufacturing an analgesic or a medicament for treating migraine;

the method comprises using a compound according to claim 1 to manufacture the analgesic or medicament.

18. A method for manufacturing an analgesic;

the method comprising using a compound according to claim 1 to manufacture the analgesic.

* * * * *